United States Patent [19]
Kim et al.

[11] Patent Number: 6,015,706
[45] Date of Patent: Jan. 18, 2000

[54] MICROORGANISM RESISTANT TO HYDROGEN PEROXIDE

[75] Inventors: In-seop Kim, Seoul; Seung-uhn Kim, Pusan; Nam-hee You; Soon-young Lee, both of Kyunjki-do, all of Rep. of Korea

[73] Assignee: Samsung Electronics Co., Ltd., Suwon, Rep. of Korea

[21] Appl. No.: 09/027,302

[22] Filed: Feb. 20, 1998

[30] Foreign Application Priority Data

Feb. 25, 1997 [KR] Rep. of Korea ................ 97-5704

[51] Int. Cl.[7] ....................................... C12N 1/20
[52] U.S. Cl. ........................................... 435/252.1
[58] Field of Search ............................. 435/252.1

[56] References Cited

U.S. PATENT DOCUMENTS 2,966,445 12/1960 Beers .................... 435/252.1
3,123,539 3/1964 Beers .................... 435/252.1

OTHER PUBLICATIONS

ATCC Catalogue of Bacteria, 1996, pp. 216–217.

*Primary Examiner*—Irene Marx
*Attorney, Agent, or Firm*—Myers Bigel Sibley & Sajovee

[57] ABSTRACT

A novel isolated microorganism, *Micrococcus luteus* KCTC 0369BP, exhibits a linear survival curve versus the concentration of hydrogen peroxide and is thus useful in a method of determining the degree of sterilization of, for example, ultrapure water that has been sterilized by hydrogen peroxide. The novel isolated microorganism produces a surface polysaccharide and a catalase.

2 Claims, 3 Drawing Sheets

0% °(○), 0.1% (●), 0.25% (▽), 0.5% (▼), 0.75% (□), 1.0% (■)

0% (○), 0.1% (●), 0.25% (▽), 0.5% (▼), 0.75% (□), 1.0% (■)

MICROORGANISM RESISTANT TO HYDROGEN PEROXIDE

FIELD OF THE INVENTION

The present invention relates to a novel, isolated microorganism that is resistant to hydrogen peroxide and is useful in methods of monitoring sterilization processes using hydrogen peroxide.

BACKGROUND OF THE INVENTION

Semiconductor manufacturing and other "clean" industries require extremely pure water such as ultra-pure water or deionized water. Numerous methods of obtaining ultra-pure water and deionized water are known in the art. For example, ultra-pure water may be obtained by a physical filtration utilizing a filter having filtering apertures of a designated level. In the preparation of deionized (DI) water, ions contained in water are separated or adsorbed either through electrochemical methods or with ion resin layers.

In addition to particulate and ionic contaminants, water used in industries such as semiconductor manufacturing is also threatened by microbial contamination. While the presence of microorganisms, per se, in otherwise clean water is not desirable, their presence is also not necessarily disastrous, in that the water is usually in contact with the semiconductor component being manufactured for such a brief amount of time that damage to the component is negligible. Far more dangerous to clean industrial processes is the presence of biofilm that may be produced by microorganisms present in, for example, ultrapure or deionized water, ultrapure water preparing apparatuses, ultrapure water piping systems, production lines or semiconductor materials in the manufacturing process. Biofilm is a gel state layer containing microorganisms growing on the boundary between liquid and solid phases in an aqueous environment (e.g., the surface of a substratum in a water piping system), and attached to the surface by aggregates of extracellular polymer substances (also referred to as exopolymer polysaccharides, or EPS) produced by the organisms. Notably, biofilm may contain a large number of microorganisms (about $10^7$ to $10^{11}$ cells/ml of biofilm mass), even though few microorganisms (as few as 1 to 10 CFU/ml) are simultaneously growing in the bordering aqueous phase.

Generally, biofilm encloses the microorganisms and primarily consists of water (70 to 95% by weight of wet weight) and an organic substance such as a polysaccharide (70 to 95% by weight of dry weight). Biofilm may be formed uniformly on the entire surface of the substratum, or may be formed in patchy patterns in thicknesses of up to about several hundreds micrometers. Since biofilm prevents the diffusion of dissolved oxygen, aerobic microorganisms contained in biofilm as thin as about 50–150 $\mu$m become anaerobic.

Unattached microorganisms present in purified water or water systems may be removed, to a certain extent, by sterilization processes known to those skilled in the art. Unfortunately, simple sterilization is not sufficient to remove attached microorganisms and the biofilm produced by such microorganisms from such environments. One reason that sterilization is ineffective in removing attached microorganisms is that physiologically inactive microorganisms are easily adsorbed onto surfaces present in aqueous environments, thus serving as additional surfaces that newly introduced microorganisms may adsorb to. Microorganisms on the surface of biofilm are difficult to kill or remove by sterilization because they form matrices with other microorganisms and the EPS produced thereby.

At present, deposits of attached microorganisms and biofilms produced thereby are removed by two primary methods: (1) chemical methods utilizing oxidizing agents, biodispersants, surfactant and enzymes to weaken the interaction between the surface of an object and the biofilm matrix; and (2) physical methods such as shear force, mechanical methods and applications of ultrasonic energy that remove microorganisms and biofilms from fouled surfaces, with chemical methods being used primarily in the semiconductor manufacturing industry. In order to be effective, biocidal agents used in chemical methods must eliminate microorganisms efficiently before a rapid multiplication of the microorganisms can occur. The agents used in such methods are preferably safe and easily handled by operators, and mild enough to prevent physical and/or chemical damage to the system being sterilized/decontaminated. Furthermore, the biocidal agents must be easily removable from the systems being sterilized, in that the agents themselves may be considered contaminants if not removed just after the sterilization.

In current practice, semiconductor manufacturing companies using chemical methods for removing biofilms from their ultrapure water supply lines usually utilize hydrogen peroxide as the biocidal agent of choice. Hydrogen peroxide decomposes into water and oxygen, and thus does not remain after the sterilization, causing little or no corrosion in the pipe lines. Although the decontamination of water supply lines would be most effective if high concentrations of hydrogen peroxide were applied to the pipelines under high temperature conditions, hydrogen peroxide is generally used at relatively low concentrations (about 1%), so as not to produce harmful gases caused by the reaction of hydrogen peroxide and organic materials. Furthermore, temperatures of about 30° C. are generally used in the hydrogen peroxide decontamination procedures because higher temperatures may cause either damage to the pipe lines themselves, or the discharge of harmful organic or inorganic materials from drainage pipes.

While offering certain advantages, the use of hydrogen peroxide as a chemical decontaminant to remove biofilm may also be problematic. Highly concentrated hydrogen peroxide is expensive, and its removal after decontamination procedures is time-consuming, often involving a complete shut-down of the manufacturing line. Moreover, there are currently no reliable standards for the use of hydrogen peroxide (e.g., standards of effective concentrations, duration and frequency of application, etc.) as a decontaminant for removing biofilm. Optical standards for sterilization/decontamination using hydrogen peroxide are difficult to determine on a systematic basis because different sterilization conditions may be required for individual production lines. When hydrogen peroxide is used to decontaminate a water supply line but it is later determined that the decontamination procedure has been ineffective, another, more toxic chemical agent such as formaldehyde must then be used to ensure sufficient decontamination. Such an additional step is costly and time consuming, but could be avoided if reliable standards for the of hydrogen peroxide could be established.

In order to monitor the efficacy of the sterilization process, numerous samples must be gathered from the ultrapure water pipe lines after each change in operating conditions in order to determine the number of surviving microorganisms (and thus the effectiveness of the decontamination procedure). After these samples are collected (e.g., by filtration, by collection from containment surfaces, or by other means known in the art), the microorganisms contained therein must then be cultured in order to accurately determine the concentration of microorganisms present in the water supply. Unfortunately, samples taken from ultrapure water systems are notoriously difficult to culture, and standard plate-count techniques applied to cultures grown from such samples may not give an accurate estimate of microbial concentration. Moreover, samples taken from nutrient-poor environments such as ultrapure water lines, if culturable at all, may take several days to weeks to grow into detectable colonies. This kind of delay is clearly not acceptable in industries such as semiconductor manufacturing, where continual and on-line control is necessary. Samples taken from water lines to monitor decontamination efficacy may be examined by microscopy in order to detect the presence of microorganisms. However, this process is not only time consuming, but also requires the presence of a concentration of microorganisms that may simply not be present in the sample, though the water line may actually be contaminated on its surfaces by biofilm.

It is apparent that standards for the effective use of hydrogen peroxide are desirable, as are methods and agents for the determination of the efficacy of a decontamination process using hydrogen peroxide. Such methods and standards could be established by using an indicator microorganism that exhibits a predictable resistance (i.e., a standardized survival curve) to hydrogen peroxide. Such an indicator microorganism would have to be an aerobic microorganism that is easily identified, analyzed, cultured and maintained. The microorganism would also have to be more strongly resistant to hydrogen peroxide than other microorganisms that are possible contaminants in, for example, an ultrapure water supply line. Finally, the indicator microorganism would be required to exhibit predictable, repeatable, and, preferably, linear survival curves against hydrogen peroxide.

Certain microorganisms such as *Bacillus stearothermophilus* NCIMB 8224 have been previously proposed as indicator microorganisms for monitoring the efficacy of hydrogen peroxide decontamination. However, a need exists for additional microorganisms that can be used for such purposes, and especially for microorganisms that exhibit linear survival curves in relation to varying concentrations of hydrogen peroxide.

SUMMARY OF THE INVENTION

An object of the present invention is to provide a novel, isolated microorganism, *Micrococcus luteus* KCTC 0369BP, which is resistant to hydrogen peroxide and exhibits a linear survival curve in varying concentrations of hydrogen peroxide, and at varying temperatures.

An additional object of the invention is to provide an isolated polysaccharide produced by the novel microorganism *M. luteus* KCTC 0369BP, which polysaccharide is useful in monitoring the efficacy of a decontamination procedure performed with hydrogen peroxide.

Yet a third object of the invention is to provide an isolated catalase produced by the novel microorganism *M. luteus* KCTC 0369BP, which catalase is useful in monitoring the efficacy of a decontamination procedure performed with hydrogen peroxide.

Additional features and advantages of the invention will be set forth in the description which follows, and in part will be apparent from the description, or may be learned by practice of the invention. The objectives and other advantages of the invention will be realized and attained by the microorganism particularly pointed out in the written description and claims hereof, as well as in the Figures.

DETAILED DESCRIPTION OF THE INVENTION

Figure 1:
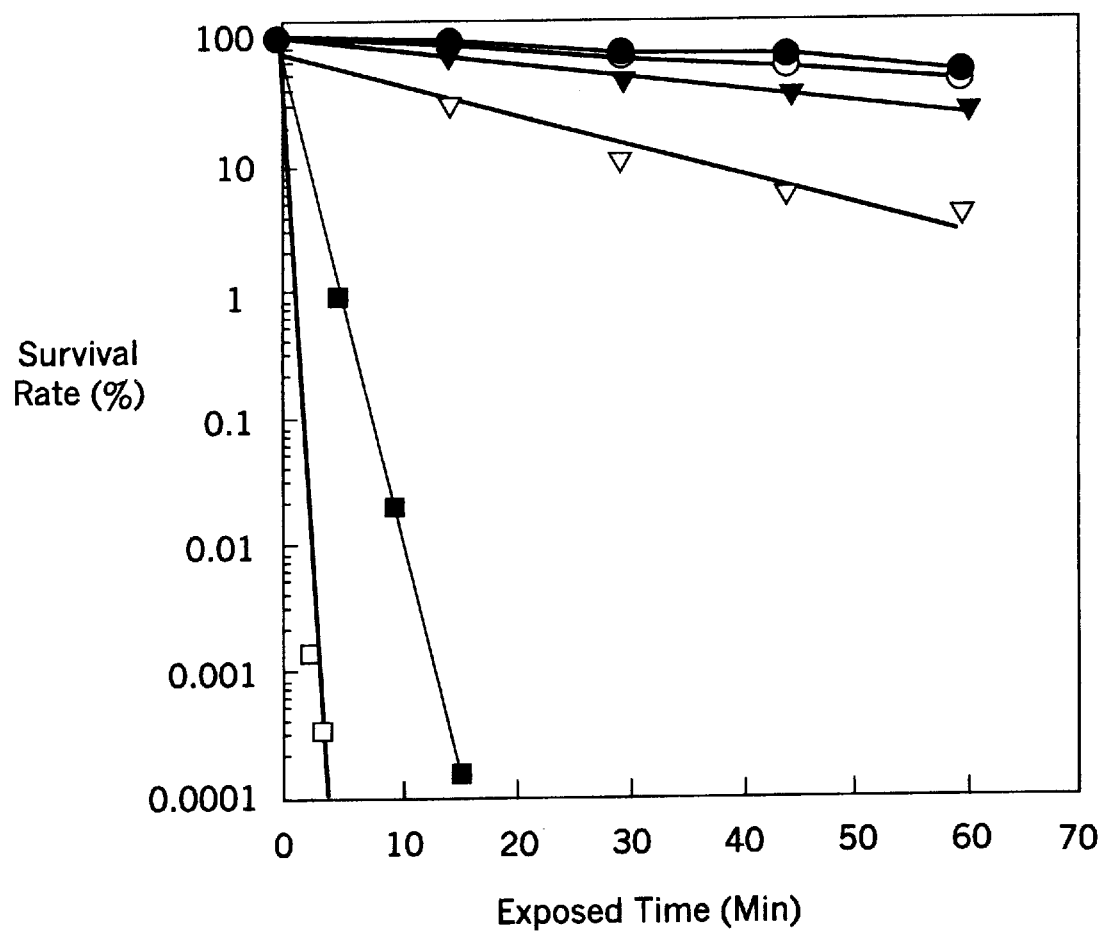
FIG. 1 is a graph obtained by plotting the survival rate of *Micrococcus luteus* KCTC 0369BP against concentrations of hydrogen peroxide of 0.5% and 1.0%, and at temperatures of 30° C., 40° C. and 50° C. Data points represent survival rates (number of microorganisms viable after hydrogen peroxide treatment, expressed as a percentage of the total amount of microorganisms) of *M. luteus* KCTC 0369BP. Solid circles represent survival rate at 30° C. in 0.5% hydrogen peroxide; open circles represent survival rate at 30° C. in 1.0% hydrogen peroxide; solid triangles represent survival rate at 40° C. in 0.5% hydrogen peroxide; open triangles represent survival rate at 40° C. in 1.0% hydrogen peroxide; solid squares represent survival rate at 50° C. in 0.5% hydrogen peroxide; open squares represent survival rate at 50° C. in 1.0% hydrogen peroxide.

Reference will now be made in detail to the preferred embodiments of the present invention, examples of which are illustrated herein.

The present invention relates to the discovery of an isolated, novel microorganism that is resistant to hydrogen peroxide. This microorganism was first deposited on Jan. 13, 1997, and then converted to a deposit under the terms of the Budapest Treaty in the Korea Research Institute of Bioscience and Biotechnology (KRIBB), Korean Collection for Type Cultures on Aug. 8 1997, and has been given the accession number KCTC 0369BP. The KRIBB is recognized as an International Depository Authority under the Budapest Treaty, and is located at #52, Oun-Dong, Yusong-Ku, Taejon 305-333, Republic of Korea. The microorganism has been analyzed and identified as a strain of *Micrococcus luteus*, and is referred to herein as *M. luteus* KCTC 0369BP. The microorganism was isolated by obtaining water samples from an ultrapure water line installed in semiconductor manufacturing factory of Samsung Electronics Company, culturing the microorganisms in nutrient broth according to methods skilled in the art, and then screening microorganisms present in the water for resistance to hydrogen peroxide, according to methods detailed herein. One microorganism exhibiting particular resistance to hydrogen peroxide was then isolated, named and deposited as *M. luteus* KCTC 0369BP.

This microorganism was analyzed and characterized with respect to its survival in varying concentrations of hydrogen peroxide and at varying temperatures. *M. luteus* KCTC 0369BP is characterized by a linear semi-logarithmic survival curve against hydrogen peroxide concentration and against temperature. Furthermore, *M. luteus* KCTC 0369BP produces a surface polysaccharide that is related to its ability to resist degradation by hydrogen peroxide. This polysaccharide may be isolated and detected according to methods which will be apparent to those skilled in the art. Finally, during its stationary growth phase, *M. luteus* KCTC 0369BP produces a large amount of catalase which may be isolated and detected according to methods known to those skilled in the art. For example, the catalase may be obtained from a suspension of the *M. luteus* KCTC 0369BP microorganism, wherein the microorganism is suspended or cultured in a medium conducive to the production of catalase, which medium may be selected from a variety of culture and growth media known to those skilled in the bacterial art. The catalase produced by the microorganisms may be separated from the cells themselves by centrifugation, at speeds which may be easily determined by the skilled artisan, but which preferably will be about 3,000 rpm. After separation from the cells, the catalase may then be concentrated by one or more of any number of general laboratory methods known to those skilled in the art such as filtration, ultrafiltration, and precipitation with salt.

The microorganism, polysaccharide, and catalase of the present invention are particularly useful in methods of monitoring the effectiveness of sterilization or decontamination procedures that utilize hydrogen peroxide. The various aspects of the present invention find particular use in, for example, monitoring sterilization and decontamination of ultrapure or deionized water supply lines, water baths, and pipes carrying ultrapure or deionized water in semiconductor manufacturing facilities, although the present invention is not limited thereto. In particular, the microorganism may be used as an indicator microorganism for such sterilization procedures. That is, since the microorganism is more resistant to hydrogen peroxide than other microorganisms that are possible contaminants in, for example. ultrapure water supply lines, the determination that the microorganism of the present invention has been completely removed from such a water supply line is a reliable indicator that all microorganisms in the line have been eliminated. Moreover, the linear and predictable semi-logarithmic survival curve exhibited by the microorganism of the present invention in varying concentrations of hydrogen peroxide and at various temperatures imparts a utility to the microorganism in establishing concentration, time and temperature standards for using hydrogen peroxide as a sterilization or decontamination agent. Finally, the polysaccharide and catalase produced by the microorganism of the present invention are similarly useful in methods of monitoring the effectiveness of sterilization with hydrogen peroxide. In that both the polysaccharide and the catalase may be detected in, for example, an ultrapure water supply line by methods known in the art, the polysaccharide and catalase are reliable indicators for the presence of the microorganism.

The following Examples are set forth to illustrate the invention, and are not intended to be limiting thereof.

EXAMPLE 1

Selection Of Microorganism

*M. luteus* KCTC 0369BP was obtained from the microorganisms present in the final UF-out ionized water and in the deionized water bath of an ultrapure line installed in a semiconductor manufacturing facility of Samsung Electronics Company (Korea). A sample of the water taken from manufacturing facility was then diluted in sterilized nutrient broth (NB) to concentrations of 1:100 and 1:10,000 (water:nutrient broth). The water diluted in the sterilized broth was cultured for three days at 30° C. After one hour at 30° C., hydrogen peroxide was added to the cultured solution to a concentration of 1% hydrogen peroxide; this solution was then cultured in an NB/100 (nutrient broth diluted 1:100) agar medium for three days at 30° C. Individual colonies of microorganisms growing in the NB/100 agar medium were serially incubated three successive times in each of NB/10 (nutrient broth diluted 1:10) and NB/100 agar media in order to select single colonies. The first 25 microorganisms selected in this manner were incubated in NB/100 and then NB/10 agar media for 18 to 30 hours. Each microorganism was then tested for hydrogen peroxide resistance as follows:

The isolated microorganisms were incubated in a rotary shaking incubator and diluted with 0.1 N phosphate buffer solution (pH 7) to a concentration of $10^8$ CFU/ml. 30 mL of the diluted microorganism solution was placed in a 50 ml conical tube. Hydrogen peroxide was added to achieve the desired concentration by volume percentage. Placing the conical tube in a constant temperature water bath at the desired temperature (e.g., 30° C., 40° C., or 50° C.), the reaction solution was analyzed at selected time intervals to determine the number of surviving microorganisms by diluting a sample of the reaction solution with a physiological saline solution and incubating the diluted sample in the nutrient broth agar medium for three days. All tests for hydrogen peroxide resistance described herein were carried out by the same method as described above.

A quantitative analysis of the survival rate of the isolated microorganisms in hydrogen peroxide as a function of the length of time treated with hydrogen peroxide was performed. The kinetic parameters analyzed were inactivation rate constant k(unit: $h^{-1}$) and D-value (unit: h). The inactivation rate constant indicates the degree of survival of the microorganism per unit hour, and is quantitatively defined by Equations 1 and 2 as follows:

$$N_2/N_1 = e^{-kt} \quad \text{[Equation 1]}$$

(where $N_1$ and $N_2$ are the numbers of microorganisms surviving at $t_1$ and $t_2$, respectively)

$$k = -1n(N_2/N_1)/(t_2-t_1) \quad \text{[Equation 2]}$$

(where $N_1$ and $N_2$ are as defined for Equation 1).

The D-value (unit: hours or h) is expressed as the amount of time required to significantly reduce the number of surviving microorganisms in hydrogen peroxide, and is quantitatively defined by Equation 3 as follows.

$$D = -1n(N_2/N_1)/k, \ N_2/N_1 = 1/10 \quad \text{[Equation 3]}$$

(where $N_1$ and $N_2$ are the numbers of microorganisms surviving at $t_1$ and $t_2$, respectively).

Of the 25 originally isolated microorganisms, the six microorganisms exhibiting the strongest resistance to hydrogen peroxide were selected. Their relative resistance to hydrogen peroxide is shown below in Table 1.

TABLE 1

The characteristics of 6 microorganisms resistant to hydrogen peroxide, taken from the microorganisms surviving in a ultrapure water.

| Microorganism Number | Nutrient broth | Gram positive | Inactivation rate constant k (h⁻¹) | D-value (h) |
| --- | --- | --- | --- | --- |
| HN-2-11 | NB | — | 0.99 | 2.33 |
| HN4-8 | NB/10 | — | 32.76 | 0.07 |
| HN4-10 | NB/10 | — | 16.91 | 0.136 |
| HN4-11 | NB/10 | — | 8.19 | 0.28 |
| HN4-12 | NB/10 | — | 13.20 | 0.174 |
| HN4-13 | NB/10 | — | 13.26 | 0.174 |

*NB = nutrient broth
NB/10 = 1:10 dilution of nutrient broth

Of the six microorganisms thus selected, HN-2-11 showed the strongest resistance to hydrogen peroxide, and was thus selected as a putative indicator microorganism for monitoring a sterilization that uses hydrogen peroxide as the biocidal agent. Microorganism HN-2-11 was identified as a strain of *Micrococcus luteus* by using the BIOLOG identification system. as KCTC 0369BP, and was deposited under the conditions of the Budapest Treaty at the Korea Research Institute of Bioscience and Biotechnology, Korean Collection for Type Cultures. HN-2-11 was given the accession number KCTC 0369BP by the International Depository Authority, and is referred to by its accession number herein.

EXAMPLE 2

Survey And Analysis For Characteristics Of Microorganism Host

*M. luteus* KCTC 0369BP, was found to exhibit a maximum proportional growth rate of 1.2448 h⁻¹ and biomass doubling time of 33.4 minutes. It also showed a linear semi-logarithmic survival curve in varying concentrations of hydrogen peroxide and at various temperatures, as illustrated in the Figures described herein. These results demonstrate that *M. luteus* KCTC 0369BP is suitable for an indicator microorganism for a sterilization with hydrogen peroxide at a low temperature.

A microphotograph was taken of the surface of *M. luteus* KCTC 0369BP prior to hydrogen peroxide sterilization and during the stationary growth phase achieved when *M. luteus* KCTC 0369BP was grown in the NB/100 agar medium for 18 hours. The microphotograph clearly showed polysaccharides produced and presented on the surface of the microorganisms, covering each microorganism and connecting the microorganisms to each other. The polysaccharides were present on the surface of the cells as protrusions about 0.4 $\mu$m long. After treatment with hydrogen peroxide, the polysaccharide protrusions disappeared from the surface of the microorganism as the survival rate of the microorganism decreased. This result indicates that the polysaccharides on the surface of *M. luteus* KCTC 0369BP are clearly related to its ability to resist hydrogen peroxide treatment.

It is known in the art that enzymes relating to the mechanism of resistance to hydrogen peroxide include catalase, peroxidase, superoxide dismutase, glucose-6-phosphate dehydrogenase, glutathion reductase and the like. Catalase, for example, is known to destroy hydrogen peroxide. See, e.g., P. J. VanDemark et al., *The Microbes* (Benjamin/Cummings Publishing Co., Menlo Park, Calif., 1987) at page 246 *M. luteus* KCTC 0369BP was found to generate a large amount of catalase in the stationary growth phase, which catalase is considered to be responsible partly for the growth cycle-dependent resistance to hydrogen peroxide.

EXAMPLE 3

Analysis For Resistance To Hydrogen Peroxide Of *M. luteus* KCTC 0369BP

Isolated *M. luteus* KCTC 0369BP was treated with hydrogen peroxide at 30° C., 40° C. and 50° C. with the concentration of hydrogen peroxide varying from 0.5% to 1%. The survival rate of *M. luteus* KCTC 0369BP under these conditions is shown in FIG. 1.

When treated with 1% hydrogen peroxide at 30° C., *M. luteus* KCTC 0369BP exhibited an inactivation rate constant k of 0.9936 h⁻¹. 38% of the initial sample of microorganism survived after 1 hour, while only 22% remained after 2 hours. Similar results were obtained for a sample of *M. luteus* KCTC 0369BP isolated from a deionized water supply line that had been treated with hydrogen peroxide. These surprising results indicate that the current method of sterilizing of one-hour sterilization with 1% hydrogen peroxide at 30° C. may actually be quite ineffective in completely eliminating the presence of microorganisms.

Figure 2:
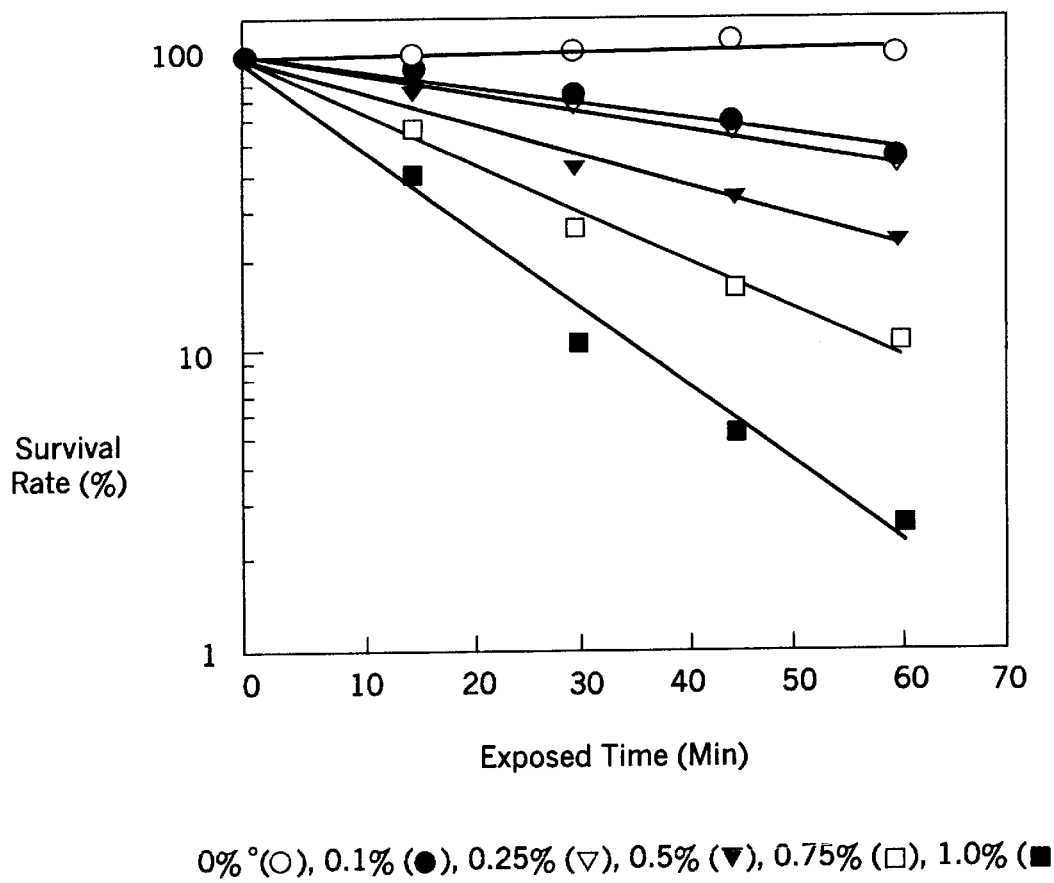
FIG. 2 is a graph obtained by plotting the survival rate (number of microorganisms viable after hydrogen peroxide treatment, expressed as a percentage of the total amount of microorganisms) of *M. luteus* KCTC 0369BP against concentrations of hydrogen peroxide of 0.1%, 0.25%, 0.5%, 0.75% and 1.0% at 40° C. Open circles represent survival rate in 0% hydrogen peroxide; closed circles represent survival rate at 0.1% hydrogen peroxide; open triangles represent survival rate at 0.25% hydrogen peroxide; closed triangles represent survival rate at 0.50% hydrogen peroxide; open squares represent survival rate at 0.75% hydrogen peroxide; closed squares represent survival rate at 1.0% hydrogen peroxide.

When *M. luteus* KCTC 0369BP was treated with hydrogen peroxide at 40° C. and 50° C., the inactivation rate constant increased proportionally with the increase in temperature. FIG. 2 shows a survival curve of *M. luteus* KCTC 0369BP at 40° C., plotted at hydrogen peroxide concentrations of 0.1%, 0.25%, 0.5%, 0.75% and 1.0%. *M. luteus* KCTC 0369BP showed a linear semi-logarithmic survival curve at all tested concentrations of hydrogen peroxide. The inactivation rate constants, in units of h⁻¹, as a function of the concentration of hydrogen peroxide are as follows: 0.9169 (0.1% hydrogen peroxide), 1.005 (0.25% hydrogen peroxide), 1.5847 (0.5% hydrogen peroxide), 2.443 (0.75% hydrogen peroxide) and 3.808 (1% hydrogen peroxide). It was further demonstrated that a sterilization with 0.25% hydrogen peroxide at 40° C. was more effective than a sterilization with 1.0% hydrogen peroxide at 30° C. In the sterilization with 1.0% hydrogen peroxide at 40° C., the inactivation rate constant was 3.808 h⁻¹ and the D-value was 0.6 h (36 minutes). These results indicate that about 97% microorganisms were destroyed by an one-hour sterilization. These results are in good agreement with the theoretical calculation that 99.999% of microorganisms will be destroyed after a one-hour, 49 minute sterilization, while 99.99951% of microorganisms will be destroyed after a two-hour sterilization. Table 2 shows the growth cycle-dependent inactivation rate constants and D-values obtained when *M. luteus* KCTC 0369BP is sterilized with 1% hydrogen peroxide at 40° C.

TABLE 2

The growth cycle dependent inactivation rate constants and D-values of *M. luteus* KCTC 0369BP during sterilization with 1% hydrogen peroxide at 40° C.

| Sampling time (h) | OD$_{500}$ | Growth phase | Inactivation rate constant k (h⁻¹) | D-value in h (minute) |
| --- | --- | --- | --- | --- |
| 4.5 | 0.27 | accelerated | 455.91 | 0.0051 (0.303) |
| 9 | 1.72 | exponential | 316.15 | 0.0073 (0.437) |
| 12 | 2.65 | reduced | 20.28 | 0.1135 (6.812) |
| 15 | 2.69 | stationary | 5.28 | 0.4202 (25.21) |
| 18 | 2.68 | stationary | 3.99 | 0.5771 (34.63) |

Figure 3:
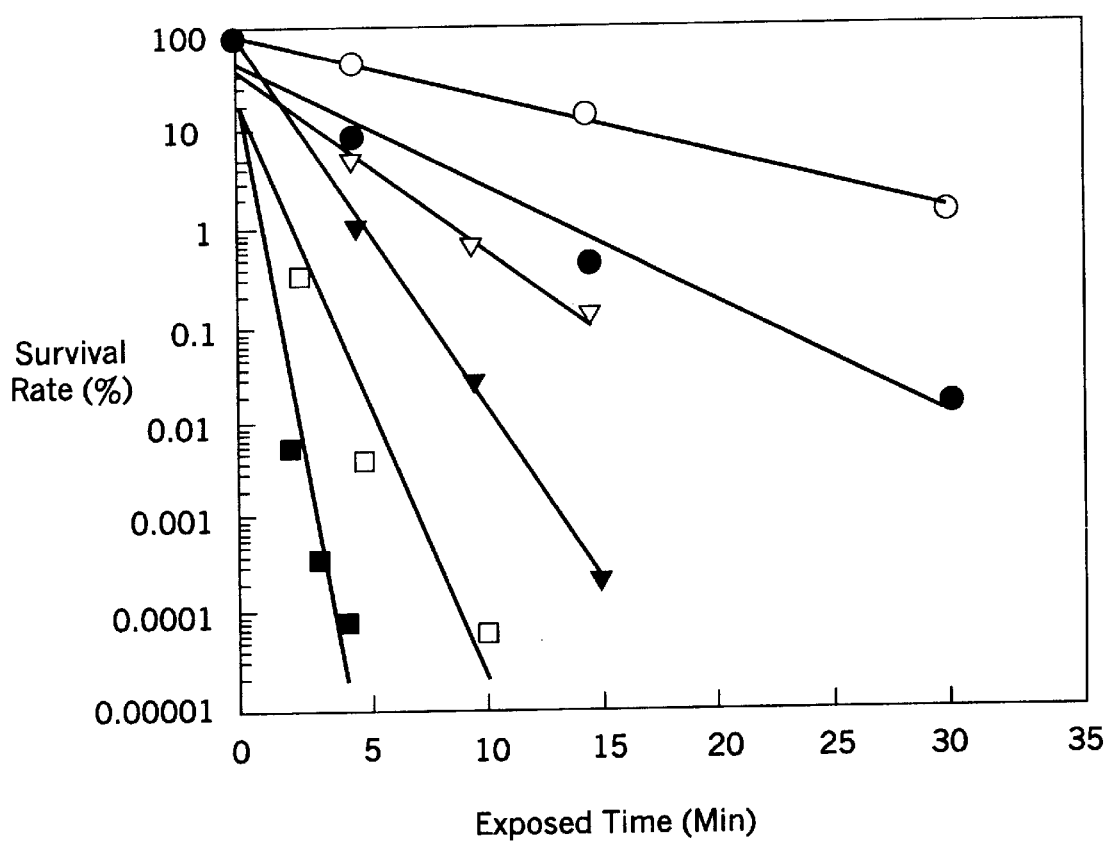
FIG. 3 is a graph obtained by plotting the survival rate (number of microorganisms viable after hydrogen peroxide treatment, expressed as a percentage of the total amount of microorganisms) of *M. luteus* KCTC 0369BP against hydrogen peroxide concentrations of 0.1%, 0.25%, 0.5%, 0.75% and 1.0%, at 50° C. Open circles represent survival rate in 0% hydrogen peroxide; closed circles represent survival rate at 0.1% hydrogen peroxide; open triangles represent survival rate at 0.25% hydrogen peroxide; closed triangles represent survival rate at 0.50% hydrogen peroxide; open squares represent survival rate at 0.75% hydrogen peroxide; closed squares represent survival rate at 1.0% hydrogen peroxide.

FIG. 3 shows a survival curve of *M. luteus* KCTC 0369BP at 50° C., plotted against hydrogen peroxide concentrations of 0.1%, 0.25%, 0.5%, 0.75% and 1.0%. At these concentrations of hydrogen peroxide, *M. luteus* KCTC 0369BP again showed a linear semi-logarithmic survival curve. The inactivation rate constants in units of $h^{-1}$ compared with concentration of hydrogen peroxide are as follows: 18.7478 (0.1% hydrogen peroxide), 28.415 (0.25% hydrogen peroxide), 53.916 (0.5% hydrogen peroxide), 86.076 (0.75% hydrogen peroxide) and 221.380 (1% hydrogen peroxide). It was demonstrated that a sterilization using 0.1% hydrogen peroxide at 50° C. was 19 times more efficient in destroying microorganisms than a decontamination using 1.0% hydrogen peroxide at 30° C. When sterilized by 0.1% hydrogen peroxide at 50° C., the inactivation rate constant was found to be 18.7478 $h^{-1}$ while the D-value was 0.123 h (7.4 minutes). These results indicate that about 99.997% microorganisms were destroyed by a 30 minute sterilization. These results are in good agreement with the theoretical calculations that 99.999% of microorganisms will be destroyed after a 22.1-minute sterilization and 99.9999999928% of microorganisms will be destroyed after an one-hour sterilization.

EXAMPLE 4

Comparison of *M. luteus* KCTC 0369BP With Other Bacteria

Table 3 shows the comparison of the inactivation rate constants and D-values between *M. luteus* KCTC 0369BP and other known microorganisms. The results shown in Table 3, illustrate that *M. luteus* 0369BP exhibits a considerably low inactivation rate constant, but a relatively high D-value.

TABLE 3

The comparison of the inactivation rate constants and D-values between *M. luteus* KCTC 0369BP and other known microorganisms.

| Microorganism | Inactivation rate constant k, ($h^{-1}$) | D-value (h) |
|---|---|---|
| *Micrococcus luteus* KCTC 0369BP | 0.99 | 2.33 |
| *Bacillus subtilis* | 44.80 | 0.05 |
| *Escherichia coli* | >230 | — |
| *Bacillus coaculus* | | |

*All values determined during hydrogen peroxide decontamination with 1% hydrogen peroxide, at 30° C.

In summary, the novel and microorganism, *Micrococcus luteus* KCTC 0369BP is resistant to hydrogen peroxide and exhibits a linear semi-logarithmic survival curve against both concentration of hydrogen peroxide and temperature. It is thus a useful indicator microorganism for monitoring sterilization procedures effected with hydrogen peroxide, and also for establishing concentration, time and temperature standards for such sterilization procedures.

In the specification and examples, there have been disclosed preferred embodiments of the invention. Although specific terms are employed in these examples, they are used in a generic and descriptive sense only and not for purposes of limitation, the scope of the invention being defined by the following claims and their equivalents.

That which is claimed is:

1. A biologically pure culture of a strain of *Micrococcus luteus* resistant to hydrogen peroxide that has a linear survival curve in relation to hydrogen peroxide concentration, having all of the identifying characteristics of *Micrococcus luteris* KCTC 0369BP.

2. The biologically pure culture of claim 1, wherein the strain is *Micrococcus luteus* KCTC 0369BP.

* * * * *